United States Patent [19]

Tohda et al.

[11] 4,345,985

[45] Aug. 24, 1982

[54] METHOD OF PRODUCING SOLID ELECTROLYTE OXYGEN-SENSING ELEMENT OF LAMINATED STRUCTURE

[75] Inventors: Masayuki Tohda, Yokosuka; Hiroshi Takao, Kamakura; Shinji Kimura, Yokohama, all of Japan

[73] Assignee: Nissan Motor Company, Limited, Yokohama, Japan

[21] Appl. No.: 219,841

[22] Filed: Dec. 23, 1980

[30] Foreign Application Priority Data

Dec. 26, 1979 [JP] Japan .................................. 54-168084

[51] Int. Cl.³ ............................................. B05D 5/12
[52] U.S. Cl. ......................... 204/192 EC; 204/192 E; 204/195 S; 427/57; 427/125; 427/126.3; 427/250; 427/255.7; 427/309; 427/376.3; 427/376.7; 427/380; 427/383.5; 427/404; 427/419.2; 134/1
[58] Field of Search ............ 427/123, 124, 125, 126.2, 427/126.3, 126.5, 57, 250, 255.7, 294, 299, 309, 376.3, 376.6, 376.7, 380, 383.5, 404, 419.2, 419.6; 204/192 C, 192 EC, 192 E, 195 S; 134/1

[56] References Cited

U.S. PATENT DOCUMENTS

| 3,978,006 | 8/1976 | Topp et al. ...................... 204/195 S |
| 4,107,019 | 8/1978 | Takao et al. ..................... 204/195 S |
| 4,126,532 | 11/1978 | Takao et al. ..................... 204/195 S |
| 4,253,931 | 3/1981 | Gold et al. ....................... 204/195 S |
| 4,253,934 | 3/1981 | Berg et al. ....................... 204/195 S |

OTHER PUBLICATIONS

Powell et al., *Vapor Deposition*, p. 236, John Wiley & Sons, Inc., N.Y., ©1966.

*Primary Examiner*—Norman Morgenstern
*Assistant Examiner*—Richard Bueker
*Attorney, Agent, or Firm*—Schwartz, Jeffery, Schwaab, Mack, Blumenthal & Koch

[57] ABSTRACT

A method of producing an oxygen sensing element which is essentially an oxygen concentration cell in the form of a lamination of relatively thin layers. The first step of the method is to prepare a lamination of a ceramic shield layer, an inner or reference electrode layer, a solid electrolyte layer and an outer or measurement electrode layer which is formed by sintering metal particles applied to the solid electrolyte layer surface in the form of a paste or slurry and dried. Then an additional measurement electrode layer, preferably not thicker than 1.0 micron, is formed on the outer surface of the sintered measurement electrode layer by a physical vapor deposition technique such as ion plating, sputtering or vacuum evaporation. Preferably this electrode layer is formed by a two-stage vapor deposition process wherein the first stage deposition is terminated before the deposited layer becomes thicker than 0.5 microns. The addition of the vapor-deposited measurement electrode layer improves the responsiveness and durability of the oxygen sensing element.

18 Claims, 36 Drawing Figures

METHOD OF PRODUCING SOLID ELECTROLYTE OXYGEN-SENSING ELEMENT OF LAMINATED STRUCTURE

BACKGROUND OF THE INVENTION

This invention relates to a method of producing an oxygen sensing element for use in a device to detect the concentration of oxygen in a gas atmosphere or to detect the air/fuel ratio of a gas mixture supplied to, e.g., an internal combustion engine based on the amount of oxygen contained in the exhaust gas, which element takes the form of a lamination of relatively thin layers including an oxygen ion conductive solid electrolyte layer, a reference electrode layer laid on one side of the solid electrolyte layer and a measurement electrode layer laid on the other side.

The usefulness of oxygen sensors of the concentration cell type utilizing an oxygen ion conductive solid electrolyte as typified by $ZrO_2$ stabilized with $Y_2O_3$ or CaO has been well appreciated in various fields.

In the current automobile industries it has been popularized to provide an oxygen sensor of this type to the engine exhaust system to detect changes in the actual air/fuel ratio of an air-fuel mixture supplied to the engine based on the amount of oxygen contained in the exhaust gas. The oxygen-sensitive element of the sensor comprises a sintered solid electrolyte layer, a measurement electrode layer formed on one side of the solid electrolyte layer so as to be exposed to a gas subject to measurement and a reference electrode layer formed on the opposite side where a reference oxygen partial pressure is to be established. These three layers constitute an oxygen concentration cell which can generate an electromotive force between the two electrode layers depending on the magnitude of an oxygen partial pressure in the gas to which the measurement electrode layer is exposed.

A recent trend is to construct this concentration cell in the form of a lamination of thin, film-like layers. For example, the solid electrolyte layer is made as thin as about 30 microns and the two electrode layers are made still thinner. The cell of the laminated construction is mounted on a thin plate of a ceramic material, which plate is called a substrate or shield layer, such that the reference electrode layer of the cell is tightly sandwiched between the shield layer and the solid electrolyte layer. Usually the concentration cell part of this element, or the entire element, is coated with a porous protecting layer of a ceramic material.

Usually the material of the reference electrode layer is a metal such as platinum or its alloy or an electronically conducting mixture of a certain metal and its oxide, such as a Ni-NiO mixture, which can serve also as the source of a reference oxygen partial pressure. A typical material of the measurement electrode layer is platinum which acts as a catalyst or its alloy.

Each of these two electrode layers is formed so as to have a microscopically porous structure usually through the steps of applying a paste containing a powdered electrode material onto the surface of the shield layer or the solid electrolyte layer by a screen-printing technique, drying the resultant paste layer and firing the unfinished element to achieve sintering of the electrode material particles applied onto the aforementioned surface.

We have recognized that hitherto developed oxygen sensing elements of the above described laminated structure type are not yet fully satisfactory in their responsiveness, that is, the amount of time delay in responding to a change in the oxygen concentration in the gas in which the element is disposed, particularly when used in automotive engine exhaust systems, and that the responsiveness is significantly related to the physical structure of the measurement electrode layer formed through a firing process as mentioned above. The firing is performed at a considerably high temperature such as about 1500° C. to achieve sufficient sintering of the electrode material applied onto the solid electrolyte layer surface by printing of a paste. Accordingly, there occurs considerable growth of the crystalline particles of the electrode material during the firing process, with the result that the measurement electrode layer is constituted of relatively coarse grains (in the microscopic sense) and therefore makes contact with a gas subject to measurement only in relatively small surface areas despite a porous structure of this electrode layer. In other words, the number and total area of so-called triple-phase points, where the solid electrolyte, measurement electrode and the gas come into contact with each other, provided by this measurement electrode layer are unsatisfactorily small relative to the macroscopic surface area of this electrode layer. By this reason, it takes a relatively large amount of time to establish an equilibrium oxygen partial pressure at the measurement electrode side of the solid electrolyte layer as the basis of generation of an electromotive force by the concentration cell, so that the oxygen sensing element does not very quickly respond to a change in the oxygen concentration in, for example, an engine exhaust gas resulting from a change in the air/fuel ratio of a gas mixture supplied to the engine.

SUMMARY OF THE INVENTION

It is an object of the present invention to provide an improved method of producing an oxygen sensing element of the above described laminated structure type having a measurement electrode layer formed on an outer surface of a solid electrolyte layer through a firing process, which method can produce such an oxygen sensing element with a greatly improved quickness of response of the element to a change in the concentration of oxygen in a gas brought into contact with the measurement electrode layer and also with improved durability in hot gas atmospheres.

In a method according to the invention for the production of an oxygen sensing element of the concentration cell type, the first step is to prepare a lamination of a shield layer formed of a ceramic material, a reference electrode layer laid on a major surface of the shield layer, an oxygen ion conductive solid electrolyte layer formed on the aforementioned surface of the shield layer such that the reference electrode layer is tightly sandwiched between the shield layer and the solid electrolyte layer and a measurement electrode layer which has a microscopically porous and gas-permeable structure and is formed on and in close contact with the outer surface of the solid electrolyte layer. In the present invention this measurement electrode layer is referred to as first measurement electrode layer and is formed by applying a wet composition containing fine particles of a metal onto the outer surface of the solid electrolyte layer, drying the applied composition to evaporate the liquid component of the composition and firing the unfinished lamination to sinter the metal particles contained in the applied composition. As the essential feature of the invention, the next step of the production method is to form a second measurement electrode layer having a microscopically porous and gas-permeable structure on the outer surface of the first measurement electrode layer by physical vapor deposition of a metal on the outer surface of the first measurement electrode layer.

The physical vapor deposition of the second measurement electrode layer can be accomplished by any one of ion plating, sputtering and vacuum evaporation techniques, and preferably the thickness of the second measurement electrode layer is made not greater than 1.0 micron.

More preferably, the second measurement electrode layer is formed by a two-stage deposition process, wherein the first stage of a physical vapor deposition process is terminated before the thickness of the deposited film exceeds 0.5 microns, and the second stage of the same physical vapor deposition process is commenced after a while and terminated before the total thickness of the resultant second measurement electrode layer exceeds 1.0 micron.

For the second measurement electrode layer use is made of a metal that catalyzes oxidation reactions of carbon monoxide and hydrocarbons, such as a metal of the platinum group or an alloy thereof.

The addition of the second measurement electrode layer formed by physical vapor deposition to the sintered first measurement electrode layer has the effect of increasing the aforementioned triple-phase points in the operation of the oxygen sensing element, and accordingly an oxygen sensing element produced by a method according to the invention is superior in the quickness of response to a change in the amount of oxygen contained in a gas subject to measurement. Therefore, this oxygen sensing element is quite suitable for use in a feedback type air/fuel ratio control system for an automotive engine and, when put into such a use, can shorten the time lag in correcting deviations of the air/fuel ratio from an intended value and, hence, can improve the accuracy of the control and facilitate purification of the exhaust gas. Besides, an improved responsiveness of this oxygen sensing element even at relatively low temperatures makes a contribution to an improvement in the controllability during a starting phase of operation of the engine under the control of the air/fuel ratio control system.

Furthermore, the combination of the first and second measurement electrode layers is superior also in the strength of adhesion to the solid electrolyte layer and in durability to a single sintered measurement electrode layer, and accordingly an oxygen sensing element produced by a method of the invention has improved durability and service life when used in hot and temperature-varying gas temperatures, such as automotive engine exhaust gases.

The present invention is applicable, though not limited, to the production of an oxygen sensing element for use in oxygen-sensing or air/fuel ratio detecting devices disclosed in U.S. Pat. Nos. 4,207,159 and 4,224,113.

BRIEF DESCRIPTION OF THE DRAWINGS

FIGS. 7(A) to 12(B) illustrate several manners of deposition of an electrode layer in a method according to the invention in partial, sectional and explanatorily enlarged views, wherein FIGS. 7(A), 7(B) and 8 are for explanation of the electrode layer formation by ion plating technique, FIGS. 11(A), 11(B), 12(A) and 12(B) are for explanation of the same by vacuum evaporation technique;

DESCRIPTION OF THE PREFERRED EMBODIMENTS

Figure 1:
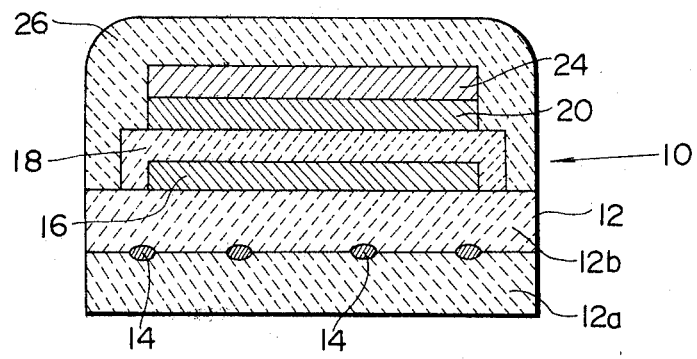
FIG. 1 is a schematic and sectional view of an oxygen sensing element produced by a method according to the present invention.

FIG. 1 shows a fundamental construction of an oxygen sensing element 10 produced by a method according to the invention. In this element 10, a structurally basic member is a base plate or substrate 12 which is made of an electrochemically inactive ceramic material. A reference electrode layer 16 is formed on a major surface of the substrate 12, and a layer 18 of an oxygen ion conductive solid electrolyte is formed on the same surface of the substrate 12 so as to closely and substantially entirely cover the reference electrode layer 16. A first measurement electrode layer 20 is formed on the outer surface of the solid electrolyte layer 18, and a second measurement electrode layer 24 is formed so as to closely cover the outer major surface of the first measurement electrode layer 20 over the entire area thereof.

Each of the solid electrolyte layer 18 and the two electrode layers 16 and 20 is a thin, film-like layer (though regarded as a "thick film" in the field of current electronic technology), so that the total thickness of these three layers is, for example, only about 70 microns or even smaller. The second measurement electrode layer 24 is a thin film preferably not greater than 1 micron in its thickness. The substrate 12 may have a thickness of about 1 mm, for example. If desired, it is possible to make the solid electrolyte layer 18 thick and rigid enough to serve as a structurally basic member of the element. In that case, the "substrate" 12 can be replaced by a thin, film-like layer of a ceramic material. In view of such a possibility, as well as a fact that macroscopically the reference electrode layer 16 is shielded from an environmental atmosphere by the substrate 12 and the solid electrolyte layer 18, in the present application the substrate 12 or a thin layer corresponding thereto is called a shield layer.

Preferably the outer surfaces of the multi-layered part of this element 10 are coated with a protecting layer 26 which is made of a ceramic material and has a porous structure to allow a gas subject to measurement to pass therethrough.

When it is intended to use the oxygen sensing element 10 even in relatively low temperature gas atmospheres as exemplified by the case of detecting the air/fuel ratios in an internal combustion engine even during a starting phase of the engine operation where the exhaust gas temperature is not sufficiently high, a heater element 14 in the form of either a thin wire or a thin layer of an electrically resistive metal is embedded in the shield layer 12 because, as an inherent property of an oxygen ion conductive solid electrolyte, at relatively low temperatures the conductivity of oxygen ions in the solid electrolyte layer 18 becomes so low that the oxygen sensing element 10 cannot properly function. In that case, the shield layer 12 may be prepared by face-to-face bonding of two sheets 12a and 12b with the interposal of the heater element 14 therebetween.

Though not shown in FIG. 1, electrical leads are connected to the reference electrode layer 16 and the first measurement electrode layer 20 to take out an electromotive force generated by an oxygen concentration cell constituted of the four layers 16, 18, 20 and 24. The heater element 14 is also provided with leads for the supply of a heating current.

The present invention does not place any particular restriction on the known materials and methods for the formation of the shield layer 12, reference electrode layer 16 and solid electrolyte layer 18.

Used for the shield layer 12 is a ceramic material such as alumina, mullite, spinel, forsterite or steatite. The shield layer 12 to serve as the substrate of the element 10 is produced, for example, by sintering of a so-called green sheet prepared by moulding or extrusion of a wet composition comprising a powdered raw material for a selected ceramic material as the principal component, by sintering of a press-formed powder material or by machining of a sintered plate of a selected ceramic material.

Typical examples of electrically resistive metals for use as the heater element 14 are Pt, W and Mo. For example, the heater element 14 can be embedded in the shield layer 12 as an assembly of the two sheets 12a and 12b by printing of a paste containing platinum powder onto a major surface of one of the two sheets 12a, 12b prior to the bonding of these two sheets 12a, 12b and subsequently sintering the printed paste layer.

As to the material for the reference electrode layer 16, a choice is made between two categories of electrode materials depending on the method of establishing a reference oxygen partial pressure at the interface between this electrode layer 16 and the solid electrolyte layer 18. Where it is intended to establish the reference oxygen partial pressure without relying on any external measure, use is made of an electronically conducting mixture of a metal and its oxide, such as Ni—NiO, Co—CoO or Cr—$Cr_2O_3$, which serves as the source of a suitable amount of oxygen within the aforementioned concentration cell. Where it is intended to establish the reference oxygen partial pressure by supplying a DC current to the concentration cell in this element 10 such that a constant current of an adequate intensity flows through the solid electrolyte layer 18 to keep oxygen ions migrating through the solid electrolyte layer 18 between the reference electrode layer 16 and the first measurement electrode layer 20 in a selected direction at an adequate rate, as proposed in U.S. Pat. Nos. 4,207,159 and 4,224,113, the reference electrode layer 16 is formed of a metal, preferably selected from metals of the platinum group such as Pt, Ru, Pd, Rh, Os and Ir, alloys of these platinum group metals and alloys of a platinum group metal with a base metal. In either case, the reference electrode layer 16 is formed so as to have a microscopically porous structure permeable to gas molecules.

For example, the reference electrode layer 16 can be formed by applying a paste containing a powdered electrode material onto the surface of the shield layer 12 by a screen-printing technique, drying the resultant paste layer and thereafter firing the dried layer.

The metal for the solid electrolyte layer 18 can be selected from oxygen ion conductive solid electrolyte materials used for conventional oxygen sensors of the concentration cell type. Some examples are $ZrO_2$ stabilized with CaO, $Y_2O_3$, SrO, MgO, $ThO_2$, $WO_3$ or $Ta_2O_5$; $Bi_2O_3$ stabilized with $Nb_2O_5$, SrO, $WO_3$, $Ta_2O_5$ or $Y_2O_3$; and $Y_2O_3$ stabilized with $ThO_2$ or CaO. In the case of the reference electrode layer 16 being formed of a metal-metal oxide mixture to serve as the source of an oxygen partial pressure, the solid electrolyte layer 18 is formed so as to have a tight structure practically impermeable to gases. In the case of establishing a reference oxygen partial pressure by the above described current-supplying method, the solid electrolyte layer 18 is formed so as to become microscopically porous and permeable to gas molecules. In the latter case, it is preferable to form the solid electrolyte layer 18 by screen-printing of a paste containing a powdered solid electrolyte material onto the shield layer 12 which has been laid with the reference electrode layer 16, drying the resultant solid electrolyte paste layer and firing the dried layer.

The first measurement electrode layer 20 is made to be microscopically porous and permeable to gas molecules. For this electrode layer 20, use is made of an electronically conducting material which is resistant to corrosion and can catalyze oxidation reactions of carbon monoxide, hydrocarbons, etc. Particularly it is suitable to use Pt or a different metal of the platinum group such as Ru, Pd, Rh, Os or Ir, or an alloy of the platinum group metals, such as Pt—Rh. This electrode layer 20 is formed by applying a wet composition, such as a paste, containing a powdered electrode material onto the outer surface of the solid electrolyte layer 18, drying the resultant metal paste layer and thereafter firing the dried layer. It is suitable to employ a screen-printing technique for the application of the wet composition.

Sintering of the shield layer 12, reference electrode layer 16, solid electrolyte layer 18 and first measurement electrode layer 20 should be effected before formation of the second measurement electrode layer 24. To meet this requirement, these four layers 12, 16, 18 and 20 may be fired individually, that is, each in a state still having an entirely exposed outer surface. Alternatively, these four layers 12, 16, 18 and 20 (and if desired the heater element 14, too) may be sintered simultaneously by first placing these layers 12, 16, 18, 20 one upon another in the described and illustrated order without firing any of them in the course of the laminating process and then subjecting the resultant multi-layered structure to a firing process which is carried out in the atmospheric air.

After formation of the sintered first measurement electrode layer 20, the uncompleted element is subjected to ultrasonic cleaning in an organic solvent as a preparatory step to the formation of the second measurement electrode layer 24.

An electronically conducting material for the second measurement electrode layer 24 can be selected from the catalytic and noncorrosive metals and alloys mentioned with respect to the first measurement electrode layer 20. This electrode layer 24 is made to be microscopically porous and permeable to gas molecules and, unlike the first measurement electrode layer 20, must be formed by a physical vapor deposition technique such as ion plating, sputtering or vacuum evaporation. The formation of this electrode layer 24 will later be described more in detail.

The porous protecting layer 26 is formed of a ceramic material such as alumina, mullite or calcium-zirconate by the employment of a plasma-spraying method by way of example.

A preferable range of the thickness of the first measurement electrode layer 20 formed through a firing process is from about 5 microns to about 15 microns, but the second measurement electrode layer 24 formed by a physical vapor deposition method is made far thinner. It is preferable that the thickness of the second measurement electrode layer 24 is not larger than 1 (one) micron. From a practical viewpoint, the minimum thickness of this layer 24 is about 0.1 micron.

Figure 2:
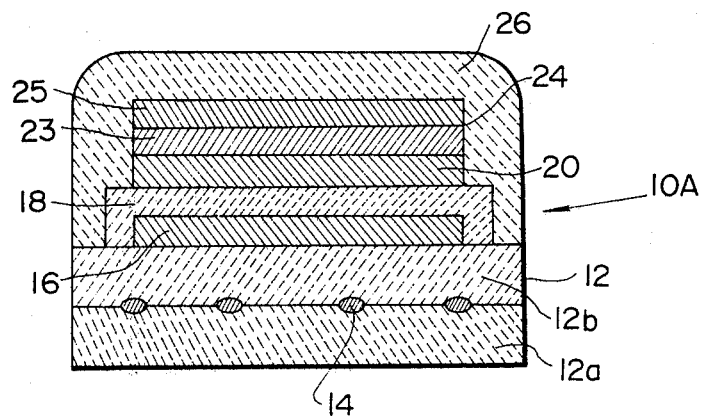
FIG. 2 is a similar view of another oxygen sensing element which is different from the element of FIG. 1 in the details of the outer electrode layer but is also produced by a method according to the invention.

The thin second measurement electrode layer 24 may be formed by a single or uninterrupted deposition operation. However, this electrode layer 24 exhibits better effects when this layer 24 is formed, as shown in FIG. 2, as a lamination of an inner layer 23 laid directly on the first measurement electrode layer 20 and an outer layer 25 which covers the inner layer 23 over the entire area by a two-stage deposition process, which may be two-stage ion plating, two-stage sputtering or two-stage vacuum evaporation, with a time interval between the two stages. The same electrode material is used for the inner and outer layers 23 and 25. In this case, it is preferable to terminate the first stage of the deposition process before the thickness of the inner layer 23 exceeds 0.5 microns. Preferably the total thickness of the inner and outer layers 23 and 25 is made not to exceed 1 micron.

If desired, the second measurement electrode layer 24 may be formed as a lamination of three or more layers by a multi-stage deposition process with time intervals between the succeeding two stages, but in practice the effects of the second measurement electrode layer 24 can be nearly maximized by the employment of the two-layered structure as illustrated in FIG. 2.

Figure 3:
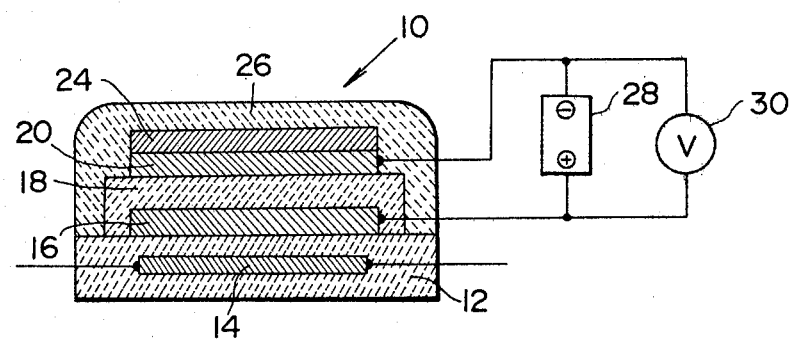
FIG. 3 shows a fundamental construction of an air/fuel ratio detecting device which utilizes the oxygen sensing element of FIG. 1.

FIG. 3 illustrates the application of an oxygen sensing element produced by a method according to the invention to a device for detecting the air/fuel ratio of an air-fuel mixture supplied to a combustor such as an internal combustion engine by sensing the concentration of oxygen in the combustion gas or exhaust gas. The fundamentals of this air/fuel ratio detector are disclosed in U.S. Pat. No. 4,207,159 and 4,224,113, but the oxygen sensing elements in these U.S. patents do not comprise an electrode layer corresponding to the second measurement electrode layer 24 according to the present invention. Illustrated in FIG. 3 is the oxygen sensing element 10 of FIG. 1, but the element 10A of FIG. 2 can also be utilized in the device of FIG. 3.

As a feature of this air/fuel ratio detecting device, a DC power source 28 is connected to the reference electrode layer 16 and the first measurement electrode layer 20 of the oxyen sensing element 10, in parallel with a voltage-measuring device 30 to measure an output voltage of the element 10, to force a constant DC current of an adequately predetermined intensity (e.g. about 10 microamperes) to flow through the solid electrolyte layer 18 between the two electrode layers 16 and 20 to thereby cause an adequate rate of migration of oxygen ions through the solid electrolyte layer 18 from selected one of the two electrode layers 16, 20 towards the other electrode layer 20, 16, while either conversion of oxygen molecules to oxygen ions or conversion of oxygen ions to oxygen molecules takes place at the catalytic measurement electrode layers 24, 20 contacting the exhaust gas and a reverse change at the reference electrode layer 16 to which diffuses the exhaust gas through the micropores in the solid electrolyte layer 18. As a joint effect of the migration of oxygen ions and diffusion of oxygen molecules in the solid electrolyte layer 18, a reference oxygen partial pressure of a suitable magnitude can be established at the interface between the reference electrode layer 16 and the solid electrolyte layer 18. For example, where the engine is operated with a lean mixture having an air/fuel ratio higher than the stoichiometric ratio the DC current is forced to flow through the solid electrolyte layer 18 from the measurement electrode layer 20 towards the reference electrode layer 16 to thereby establish and maintain a reference oxygen partial pressure of a relatively small magnitude at the aforementioned interface in the element 10.

When the oxygen sensing element 10 is designed so as to establish a reference oxygen partial pressure therein by utilizing a mixture of, for example, Ni and NiO as the material of the reference electrode layer 16, a device analogous in purpose to the device of FIG. 3 is constructed without the provision of the DC power supply 28. However, the device of FIG. 3 is advantageous in having the ability of exactly detecting numerical values of the air/fuel ratio of either a lean mixture or a fuel-rich mixture.

Figure 4:
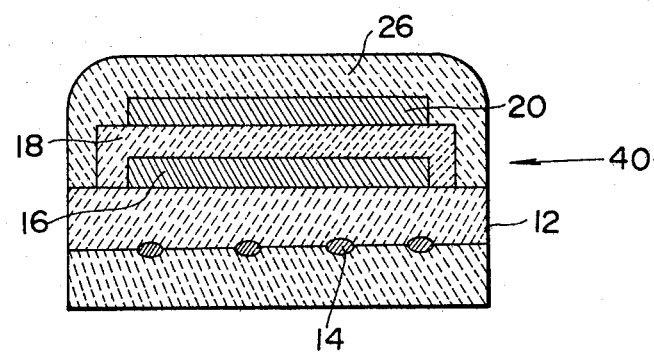
FIG. 4 is a schematic and sectional view of an oxygen sensing element which resembles the element of FIG. 1 but is the product of a method not in accordance with the invention.

FIG. 4 shows an oxygen sensing element 40, which resembles the element 10 of FIG. 1 and functions on the same principle but is produced by a hitherto employed method. As can be seen and as described hereinbefore, in this element 40 the measurement electrode layer 20 formed through a firing process is coated directly with the protecting layer 26, or it can be said that this electrode layer 20 is exposed directly to an environmental gas atmosphere by disregarding the porous and unessential protecting layer 26.

Figure 6A:
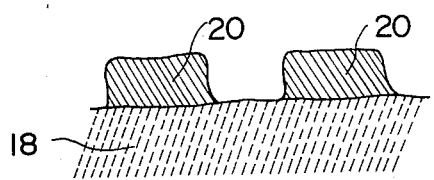
FIG. 6(A) is a partial, sectional and explanatorily enlarged view of an electrode layer formed by an intermediate step of a production method according to the invention.

The fundamental reasons for the formation of the second measurement electrode layer 24 according to the invention will be explained with reference to the explanatory illustrations in FIGS. 6(A) and 6(B).

The first measurement electrode layer 20 is formed through a firing step which is carried out at a temperature as high as about 1500° C. to achieve complete sintering of the electrode material such as platinum applied onto the surface of the solid electrolyte layer 18 in the form of wet particles and then dried. This electrode layer 20 must be formed so as to have a microscopically porous structure, but the pores in this layer 20 need not to be very large in their cross-sectional area. During the high temperature sintering process, however, there occur coagulation of the electrode material particles and growth of the crystalline particles under sintering to result in that the first measurement electrode layer 20 is constituted of considerably coarse metal grains with relatively large gaps therebetween as illustrated in FIG. 6(A). Therefore, a considerably large part of the surface area of the solid electrolyte layer 18 is left exposed in the pores of this electrode layer 20. This means that the number and the total area of the so-called triple-phase points, where the solid electrolyte 18, measurement electrode 20 and a gas subject to measurement come into contact with each other, becomes undesirably small relative to the macroscopical surface area of the electrode layer 20. For this reason, the catalytic ability of the measurement electrode layer 20 can be exhibited only to a small extent, so that the oxygen sensing element becomes unsatisfactory in the quickness of its response to a change in the composition of the gas brought into contact with the measurement electrode layer 20.

Figure 6B:
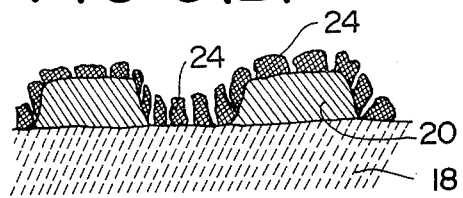
FIG. 6(B) is a similar view of another electrode layer formed on the electrode layer of FIG. 6(A) by the next step of the same production method.

Referring to FIG. 6(B), the second measurement electrode layer 24 formed by a physical vapor deposition method is constituted of very small particles of the selected metal and intrudes into the pores in the first measurement electrode layer 20 to cover a large part of the exposed areas of the solid electrolyte surface 18. Of course, this layer 24 serves both as an electrode and as a catalyst similarly to the first measurement electrode layer 20. That is, from a functional viewpoint the lamination of the first and second measurement electrode layers 20 and 24 in an oxygen sensing element produced by the present invention can be regarded as a single measurement electrode layer. The addition of the second measurement electrode layer 24 as illustrated in FIG. 6(B) to the first measurement electrode layer 20 results in a great increase in the number and the total area of the aforementioned triple-phase points in the oxygen sensing element. During operation of the resultant oxygen sensing element, catalytic reactions occur more vigorously and smoothly at the laminated measurement electrode layer (20+24) than in the case of the sintered measurement electrode layer 20 alone, and therefore this oxygen sensing element responds very quickly to changes in the composition of the gas subject to measurement.

If attention is paid solely to the quickness of the response, it is conceivable to omit the sintered measurement electrode layer 20 by forming a single measurement electrode layer by a physical vapor deposition method directly on the outer surface of the solid electrolyte layer 18. In fact, an oxygen sensing element produced in this way exhibits an improved responsiveness compared with the known oxygen sensing element 40 of FIG. 4, but there arises a serious problem that the durability of the measurement electrode layer in hot and temperature-varying gas atmospheres lowers so greatly that the oxygen sensing element becomes almost impractical. Besides, in the case of providing the protecting layer 26 to the oxygen sensing element not having the sintered measurement electrode layer 20 it becomes difficult to realize sufficiently strong or durable adhesion of the protecting layer 26 to the element. Therefore, the present invention proposes to add the newly conceived electrode layer 24 to the conventionally employed measurement electrode layer 20.

EXAMPLE 1

FIGS. 5(A) to 5(H) illustrate a process employed in this example to produce an oxygen sensing element 10A which had the construction illustrated in FIG. 2 and designed so as to serve for an air/fuel ratio detecting device of the type shown in FIG. 3.

Figure 5A:
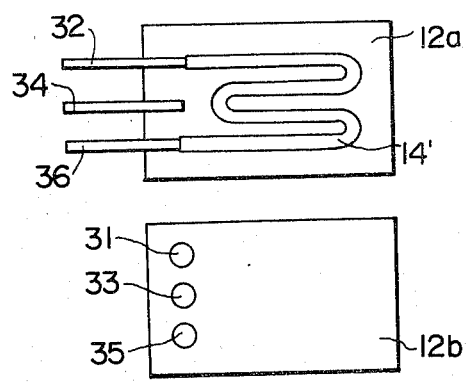
FIGS. 5(A) to 5(H) illustrate an exemplary process of producing the oxygen sensing element of FIG. 2 by a method according to the invention.
Figure 5B:
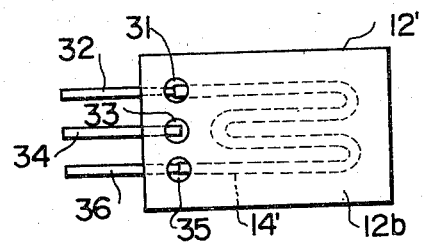

Referring to FIGS. 5(A) and 5(B), an alumina green sheet 12a (formed of a wet alumina-base composition, 5×9 mm wide and 0.7 mm thick) and another sheet 12b which was similar in material and dimensions to the former sheet 12a but was formed with three through-holes 31, 33, 35 were used to constitute an unfired shield layer 12'. As shown in FIG. 5(A), three platinum wires 32, 34, 36 (0.2 mm in diameter) were partly placed on the alumina green sheet 12a in an arrangement corresponding to the holes 31, 33, 35 of the other sheet 12b, and a paste containing platinum powder was applied onto the surface of the same sheet 12a by a screen-printing technique to form a paste layer 14' which was elongate and meandering in plan view shape and terminated at the tip portions of the platinum wires 32 and 36. After drying of this paste layer 14', the bored sheet 12b was placed on the former sheet 12a such that the tip portions of the three wires 32, 34, 36 were located just beneath the three through-holes 31, 33, 35, respectively, as can be seen in FIG. 5(B), and the two sheets 12a, 12b in this state were adhered to each other by the application of a pressure of about 10 kg/cm$^2$ to give the unfired shield layer 12', which had been provided with leads 32, 34, 36 and the platinum layer 14' to become the heater element 14 in FIG. 2 through a subsequent firing process.

Figure 5C:
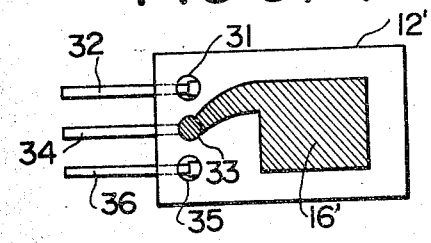

Then, a platinum paste, which was a dispersion of 70 parts by weight of platinum powder in 30 parts by weight of a lacquer comprising a resin binder and an organic solvent, was applied onto an outer surface of the unfired shield layer 12' (the outer surface of the bored sheet 12b) by a screen-printing technique so as to form a paste layer 16' as shown in FIG. 5(C). This paste layer 16' was made to locally extend to the hole 33 in the shield layer 12' to fill up this hole 33 with the platinum paste and dried before the next procedure.

Figure 5D:
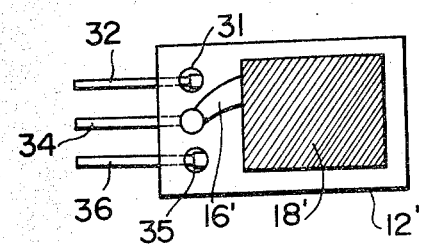

Next, a solid electrolyte paste prepared by dispersing 70 parts by weight of powdered $ZrO_2$—$Y_2O_3$ (95:5 mole ratio) in 30 parts by weight of a lacquer was applied onto the outer surface of the dried platinum layer 16' by screen-printing so as to form a paste layer 18', as shown in FIG. 5(D), and dried. As the result, the platinum layer 16' was substantially entirely (except) the elongate part extending to the hole 33: this part can be regarded as part of a lead) covered by the solid electrolyte layer 18', which had not yet been fired.

Figure 5E:
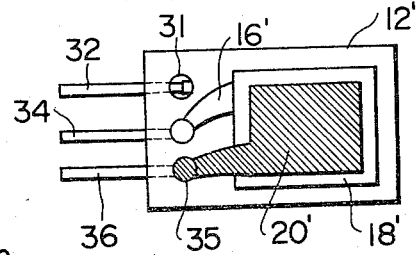

Thereafter the platinum paste used to form the platinum layer 16' was applied onto the outer surface of the dried but unfired solid electrolyte layer 18' by screen-printing so as to form a platinum paste layer 20', as shown in FIG. 5(E), which was made to locally extend to the hole 35 in the unfired shield layer 12' to fill up this hole 35 with the platinum paste.

After drying of the outermost platinum paste layer 20', the multi-layered article in the state of FIG. 5(E) was subjected to a firing process which was carried out in the atmospheric air at a temperature of 1500° C. for a period of 2 hours to achieve simultaneous sintering of all the layers 12', 14', 16', 18' and 20'. As the result, the platinum layer 16', solid electrolyte layer 18' and platinum layer 20' turned respectively into the reference electrode layer 16, solid electrolyte layer 18 and first measurement electrode layer 20 in FIG. 2. Simultaneously the unfired shield layer 12' turned into the rigid shield layer 12, and the platinum layer 14' in the shield layer turned into the heater 14. After the firing process, the reference electrode layer 16 and the first measurement electrode layer 20 were both about 10 microns in thickness, and the solid electrolyte layer 18 had a thickness of about 40 microns.

Figure 5F:
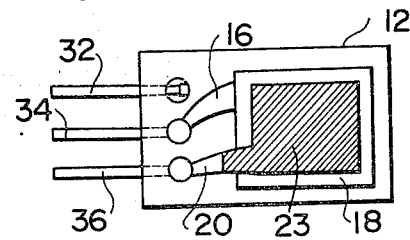

Referring to FIG. 5(F), the inner layer 23 of the second measurement electrode layer 24 in FIG. 2 was formed by depositing platinum on the outer surface of the fired first measurement electrode layer 20 by ion plating, preceded by ultrasonic cleaning of the fired but unfinished element in an organic solvent.

The already fired and cleaned element was placed in a conventional ion plating apparatus, using a mask apertured to achieve the deposition of a film in a pattern as shown by the hatched area in FIG. 5(F), that is, to deposit platinum over substantially the entire surface area of the first measurement electrode layer 20. Initially the vacuum chamber in the apparatus was pumped out to a high vacuum greater than $5 \times 10^{-6}$ Torr, and thereafter oxygen gas was introduced into the chamber until the magnitude of vacuum became in the range from $2 \times 10^{-3}$ to $1 \times 10^{-2}$ Torr. The purpose of creating the initial high vacuum is to prevent intrusion of impurities, particularly impurities attributed to a residual gas, into the deposited layer 23. This purpose can be accomplished by initially evacuating the chamber to a vacuum greater than $1 \times 10^{-5}$ Torr. It is possible to use an oxygen-argon mixed gas in place of the aforementioned oxygen gas. In either case the outer surface of the first measurement electrode layer 20, including the surfaces of the micropores in this layer 20, and the solid electrolyte surface exposed in the same micropores are cleaned and rendered activated by ion bombardment with oxygen ions originating in the introduced gas. Besides, the presence of oxygen in the chamber produces a favorable effect on the manner of growth of the deposited metal layer 23.

The range of vacuum, $2 \times 10^{-3}$ to $1 \times 10^{-2}$ Torr, after the introduction of $O_2$ or $O_2$—Ar gas was determined because it becomes difficult to realize glow discharge when the magnitude of vacuum is excessively high and also because in an unduly low vacuum there arise various problems such as oxidation contamination of the chamber by reason of an increased quantity of oxygen in the chamber, intrusion of the introduced gas into the deposited metal layer 23 and lowering of the productivity by reason of scattering of the evaporated and ionized electrode material by the gas molecules.

After the introduction of oxygen gas in this manner, an electric field was produced in the chamber to cause glow discharge, and then the evaporator filament (Pt) was energized to commence deposition of platinum film 23 on the first measurement electrode layer 20.

When the thickness of the deposited film, i.e. inner layer 23 of the second measurement electrode layer 24, became close to but smaller than 0.5 microns, the evaporator filament was deenergized, whereas the oxygen gas introduced into the chamber and the electric field for glow discharge were maintained unchanged. Accordingly, the deposited platinum layer 23 was subjected to ion bombardment.

Figure 5G:
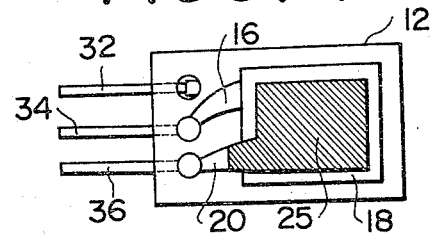

After a while the evaporator filament was again energized to deposit another platinum film as the outer layer 25 of the second measurement electrode layer 24, as shown in FIG. 5(G). This operation was terminated when the total thickness of the inner and outer layers 23, 25 of the second measurement electrode layer 24 become about 0.8 microns.

Figure 5H:
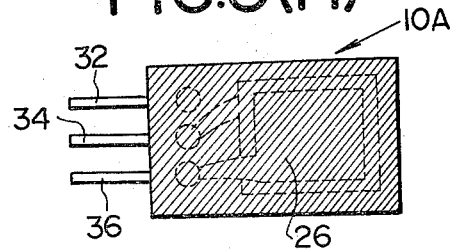

Referring to FIG. 5(H), the fabrication of the oxygen sensing element 10A was completed by plasma-spraying of a calcium-zirconate ($CaO-ZrO_2$) powder onto the frontside outer surfaces of the element in the state of FIG. 5(G) to form a gas-permeably porous protecting layer 26 which was 80–100 microns in thickness. In this element 10A the lead wires 34 and 36 are used to supply a constant DC current to the oxygen concentration cell formed in this element 10A, and the leads 32 and 36 are used to supply a heating current to the heater element 14. That is, the lead wire 36 is used as a ground lead common to the cell and the heater 14.

As will be understood, the known oxygen sensing element 40 of FIG. 4 can be obtained by excluding the vapor deposition steps of FIGS. 5(F) and 5(G) from the process illustrated by FIGS. 5(A) to 5(H).

EXAMPLE 2

In accordance with Example 1 the steps illustrated by FIGS. 5(A) to 5(E) were performed, and the multi-layered article in the state of FIG. 5(E) was subjected to the firing process described in Example 1.

After ultrasonic cleaning in an organic solvent and drying, the fired but yet uncompleted element was placed in a conventional sputtering apparatus, using a mask apertured to achieve the deposition of a film in a pattern as shown by the hatched area in FIG. 5(F). Initially the vacuum chamber of the apparatus was pumped out to a high vacuum greater than $5 \times 10^{-5}$ Torr to minimize a residual gas, and thereafter argon gas was introduced into the chamber until the pressure in the chamber became in the range from $2 \times 10^{-3}$ to $1 \times 10^2$ Torr. This range of vacuum after the introduction of Ar gas was determined for the same reason as explained in Example 1 with regard to the oxygen-containing gas atmosphere.

After the introduction of Ar gas in this manner, an electric power of 0.15–0.2 A and 1.0–1.5 KV was applied to the sputtering electrodes to commence deposition of platinum employed as the target material in this example on the first measurement electrode layer 20.

When the thickness of the deposited platinum film, i.e. the inner layer 23 of the second measurement electrode layer 24 became 0.4 microns, the sputtering operation was terminated. The element in the state of FIG. 5(F) was taken out of the sputtering apparatus and subjected to a heat treatment in the atmospheric air for a period of 1 hour at a temperature slightly lower than 1100° C.

The purposes of this heat treatment are: (a) to remove physical strains in the deposited platinum layer 23; (b) to form a sort of nuclei in the same layer 23 so that the subsequent deposition by sputtering of the outer layer 25 may be accomplished readily and with high adhesion strength between the inner and outer layers 23 and 25; and (c) to enable the deposition of the outer layer 25 in a favorable configuration. If the thickness of the deposited inner layer 23 is larger than 0.5 microns it becomes difficult to attain the effects (a), (b) and (c) of the heat treatment. If the heat treatment temperature exceeds 1100° C. these effects (a), (b), (c) can hardly be attained, either, and heat treatment at such a high temperature causes evaporation of the deposited metal layer 23. Furthermore, the temperature at the heat treatment greatly influences the quickness of response of the produced oxygen sensing element. It was confirmed that the best result from every point of view can be obtained by performing the mentioned heat treatment in air at a temperature in the range from 900° C. to 1100° C. for a period of about 1 hour.

After the heat treatment, the element in the state of FIG. 5(F) was cooled and subjected to ultrasonic cleaning in an organic solvent and then dried.

The cleaned element was again placed in the sputtering apparatus, using the aforementioned mask, and the sputtering operation under the above described conditions was resumed to deposit another platinum film as the outer layer 25 of the second measurement electrode layer 24, as shown in FIG. 5(G). This operation was terminated when the total thickness of the inner and outer layers 23, 25 of the second measurement electrode layer became about 0.8 microns. Preferably the thickness of the outer layer 25 formed by the second stage of sputtering operation is made not to exceed 0.8 microns and the total thickness of the second measurement electrode layer (23+25) is made not to exceed 1.0 micron. (The initially deposited metal layer 23 tends to reduce its thickness during the above described heat treatment.)

The production of the oxygen sensing element was completed by forming the porous protecting layer 26 in the manner as described in Example 1 and illustrated in FIG. 5(H).

EXAMPLE 3

The steps illustrated by FIGS. 5(A) to 5(E) were performed in accordance with Example 1, and the multi-layered article in the state of FIG. 5(E) was subjected to the firing process described in Example 1.

After ultrasonic cleaning in an organic solvent, the fired but yet uncompleted element was placed in a conventional apparatus for vacuum evaporation operation, using a mask apertured to achieve the deposition of a film in a pattern as shown by the hatched area in FIG. 5(F). Initially the vacuum chamber of the apparatus was pumped out to a high vacuum greater than $5 \times 10^{-6}$ Torr to minimize unfavorable influences of a residual gas. This object can be accomplished by initially establishing a vacuum greater than $1 \times 10^{-5}$ Torr. Then oxygen gas was introduced into the vacuum chamber until the pressure in the chamber became $2 \times 10^{-3}$ Torr. Prior to evaporation of platinum, an electric field was produced in the vacuum chamber containing oxygen gas to cause glow discharge to thereby perform sputter-etching of the outer surface of the sintered first measurement electrode layer 20 and the solid electrolyte surface exposed in the pores of the first measurement electrode layer 20. It is possible to use an oxygen-argon mixed gas in place of pure oxygen gas. By performing sputter-etching using an oxygen-containing gas, it is possible to activate the afore-mentioned surfaces of the first measurement electrode layer 20 and the solid electrolyte layer 18. The quantity of either oxygen gas or oxygen-argon gas is controlled such that the resultant pressure in the vacuum chamber is in the range from $2 \times 10^{-3}$ to $1 \times 10^{-2}$ Torr because it becomes difficult to realize glow discharge in an excessively high vacuum and also because the efficiency of the sputter-etching lowers at a smaller magnitude of vacuum by reason of scattering of ions by the gas molecules.

After the sputter-etching operation the chamber was again pumped out to a high vacuum greater than $1 \times 10^{-5}$ Torr to discharge the contaminating impurity substances struck out by the sputter-etching to thereby avoid intrusion of such impurities into the electrode layer to be formed by the subsequent evaporation operation. Then the heater for the evaporant source (Pt in this example) was energized to commence deposition of platinum on the etched surface of the first measurement electrode layer 20. The rate of deposition was about 3 angstroms per second.

The heater was deenergized when the thickness of the deposited platinum film, i.e. the inner layer 23 of the second measurement electrode layer 24 became close to but smaller than 0.5 microns. The element in the state of FIG. 5(F) was taken out of the vacuum chamber and subjected to a heat treatment in the atmospheric air for a period of 1 hour at a temperature of 1000° C. The purposes of this heat treatment are similar to the purposes of the heat treatment mentioned in Example 2. If the deposited layer 23 is thicker than 0.5 microns it becomes difficult to attain the expected effects of the heat treatment. This heat treatment should be performed in air for about 1 hour at a temperature in the range from 900° C. to 1100° C. The employment of a heat treatment temperature higher than 1100° C. causes a great (and undesirable) enhancement of the rate of growth of the crystalline particles of the sintered measurement electrode layer 20 and, hence, a great decrease of the aforementioned triple-phase points which determine the responsiveness of the oxygen sensing element. Besides, the heat treatment at such a high temperature causes evaporation of the deposited metal layer 23. On the other hand, the effects (b) and (c) of the heat treatment mentioned in Example 2 can hardly be attained at temperatures below 900° C.

After the heat treatment, the element in the state of FIG. 5(F) was subjected to ultrasonic cleaning in an organic solvent and thereafter dried.

The cleaned element was again placed in the vacuum evaporation apparatus, and the vacuum evaporation operation under the above described condition was resumed to deposit another platinum film as the outer layer 25 of the second measurement electrode layer 24, as shown in FIG. 5(G). This operation was terminated when the total thickness of the inner and outer layers 23 and 25 reached 0.8 microns. Since the inner layer 23 reduced its thickness to about 0.2 microns during the heat treatment (because of evaporation of a certain portion thereof and coagulation of its platinum particles), the outer layer 25 had a thickness of about 0.6 microns. Also in the case of forming the second measurement electrode layer (23+25) by vacuum evaporation, preferably the thickness of the outer layer 23 is made not to exceed 0.8 microns and the total thickness of this electrode layer 24 is made not to exceed 1.0 micron.

As the final step, the porous protecting layer 26 was formed in the manner as described in Example 1 and illustrated in FIG. 5(H).

The advantageousness of forming the second measurement electrode layer 24 as a lamination of the inner and outer layers 23 and 25 by any one of the two-stage deposition methods employed in Examples 1–3 will further be explained.

(1) Two-stage Ion Plating

Figure 7A:
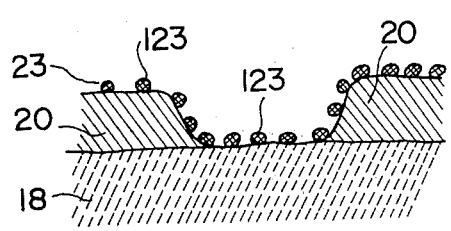

Referring to FIG. 7(A), when the inner layer 23 is formed by ion plating by using either oxygen gas or oxygen-argon gas to have a thickness not larger than 0.5 microns and then maintained in the low pressure gas atmosphere with continued glow discharge but without energizing the evaporator filament, this layer 23 takes the form of a relatively loose aggregation of a multiplicity of very tiny metal grains 123 each of which serves as a sort of nucleus at the subsequent stage of forming the outer layer 25. This state of the deposited film 23 is called "island stage" or "island structure". Presumable causes for such a structure of the deposited inner layer 23 may be that the surfaces of the first measurement electrode layer 20 and the solid electrolyte layer 18 subjected to ion bombardment are locally so heated as to allow the deposited metal particles to move on these surfaces and that the growth of the deposited metal particles is difficult to proceed in an oxygen-containing gas atmosphere.

Figure 7B:
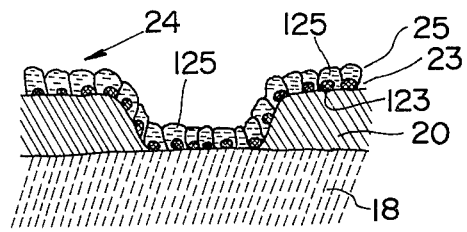

By performing the second stage ion plating operation to deposit the outer layer 25 on the inner layer 23 of which the structure is as explanatorily shown in FIG. 7(A), it is possible to obtain the outer layer 25 as an agglomeration of "columns" 125, as shown in FIG. 7(B). Each of the tiny grains 123 of the inner layer 23 becomes the nucleus of each columnar region 125 of this layer 25. The second measurement electrode layer 24 constituted of the illustrated inner and outer layers 23, 25 can provide a sufficiently large number of triple-phase points where this electrode layer 24, solid electrolyte layer 18 and a gas subject to measurement come into contact with each other and therefore can fully exhibit its catalytic property. Accordingly an oxygen sensing element having this second measurement electrode layer becomes superior in the quickness of response. A principal reason for the preferableness of limiting the total thickness of the second measurement electrode layer 24 to 1.0 micron is that it becomes difficult to realize a large number of triple-phase points as the thickness of this layer 24 increases beyond 1.0 micron. Moreover, the second measurement electrode layer 24 shown in FIG. 7(B) adheres to the first measurement electrode layer 20 and the solid electrolyte layer 18 with a remarkably high adhesion strength.

Figure 8:
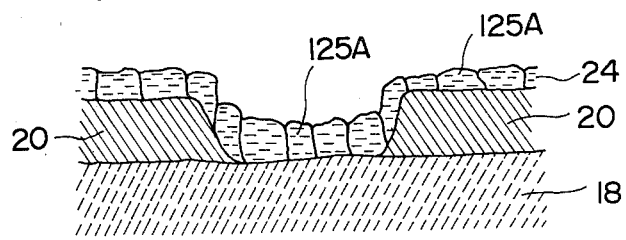

Referring to FIG. 8, when the second measurement electrode layer 24 is formed by a single-stage ion plating operation, this layer 24 becomes an agglomeration of relatively large columns 125A because of the absence of tiny grains to serve as nucleis. An oxygen sensing element having the coarse columnar second measurement electrode layer 24 of FIG. 8 can provide an increased number of triple-phase points, and therefore is quicker in response, than an analogous element not having the second measurement electrode layer but remains inferior to the element having the double-layered second measurement electrode layer 24 of FIG. 7(B).

(2) Two-stage Sputtering

Figure 9A:
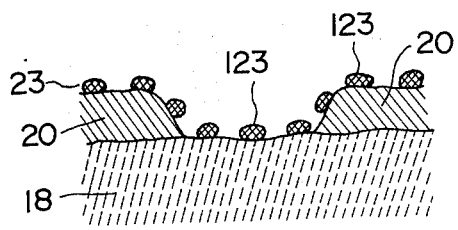
FIGS. 9(A), 9(B), 10(A) and 10(B) are for explanation of the same by sputtering technique.

Referring to FIG. 9(A), when the inner layer 23 of the second measurement electrode layer is formed by sputtering to have a thickness not larger than 0.5 microns and then subjected to the above described heat treatment, this layer 23 becomes free from internal strains and takes the form of a loose aggregation of a multiplicity of tiny grains or island-like regions 123. If the inner layer is made thicker than 0.5 microns and then subjected to the heat treatment, this layer does not remain in an island stage and becomes an almost continuous layer 123A as shown in FIG. 9(B).

Figure 10A:
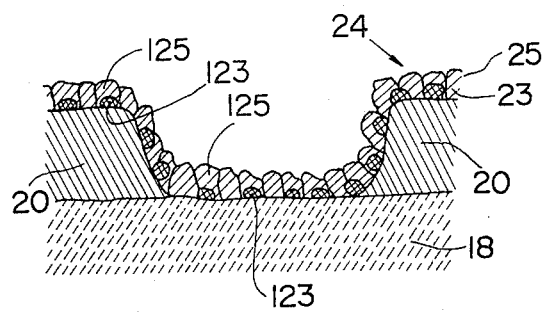

By performing the second stage sputtering operation to deposit the outer layer 25 on the inner layer 23 having the island structure as shown in FIG. 9(A) the outer layer 25 can be obtained as an agglomeration of small columns 125 as shown in FIG. 10(A), because the tiny grains 123 of the inner layer 23 serve as the nuclei for the respective columns 125. The second measurement electrode layer 24 of FIG. 10(A) and an oxygen sensing element having this electrode layer 24 exhibit the same advantages as explained above with respect to the double-layered electrode layer 24 of FIG. 7(B).

Figure 9B:
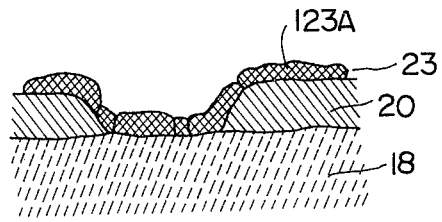
Figure 10B:
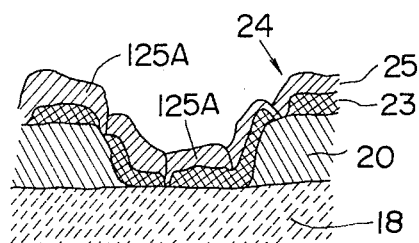

When the second stage sputtering operation is performed to deposit the outer layer 25 on the relatively thick inner layer 123A of FIG. 9(B), the outer layer 25 becomes an agglomeration of considerably large columns 125A as shown in FIG. 10(B). As will be understood the second electrode layer 24 of FIG. 10(B) is inferior in its effects to the corresponding electrode layer 24 of FIG. 10(A). That is, the addition of the second measurement electrode layer 24 of FIG. 10(B) to the usual first measurement electrode layer 20 brings about a certain increase in the triple-phase points but, in practice, does not remarkably improve the responsiveness of the oxygen sensing element.

Even in the desirable case of FIG. 10(A), it is important to avoid depositing the outer layer 25 to an unnecessarily large thickness because the formation of a thickly deposited outer layer, which is good at adhering and covering properties as the feature of a film formed by sputtering, becomes obstructive to the realization of the triple-phase points. Therefore, the deposition of this outer layer 25 is terminated before the total thickness of the second measurement electrode layer 24 (23+25) exceeds 1.0 micron.

(3) Two-stage Vacuum Evaporation

The sputter-etching procedure using either oxygen or oxygen-argon gas has the effect of affording the second measurement electrode layer 24 formed by the subsequent vacuum evaporation a remarkably high strength of adhesion to the first measurement electrode layer 20. Because, certain impurities adhered to the surface of the first measurement electrode layer 20 and the solid electrolyte surface exposed in the pores of this electrode layer 20 and hardly removable even by ultrasonic cleaning can be removed by renewal of these surfaces by the sputter-etching, and at the same time these surfaces are made suitably rough in a microscopical sense. Moreover, these surfaces are activated by bombardment with ions formed by ionization of oxygen molecules in the employed gas atmosphere.

Also in the case of forming the second measurement electrode layer 24 by a single-stage vacuum evaporation operation, it is preferable to perform the above described sputter-etching preparatorily to the evaporation operation.

Figure 11A:
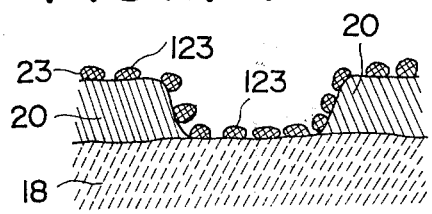

Referring to FIG. 11(A), when the inner layer 23 of the second measurement electrode layer is formed by vacuum evaporation, preceded by the described sputter-etching, to have a thickness not larger than 0.5 microns and then subjected to the hereinbefore described heat treatment, this layer 23 becomes free from internal strains and takes the form of a loose aggregation of a multiplicity of tiny grains or island-like regions 123. If the inner layer 23 is made thicker than 0.5 microns and then subjected to the same heat treatment, this layer does not remain in an island stage and becomes an almost continuous layer 123A as shown in FIG. 11(B).

Figure 12A:
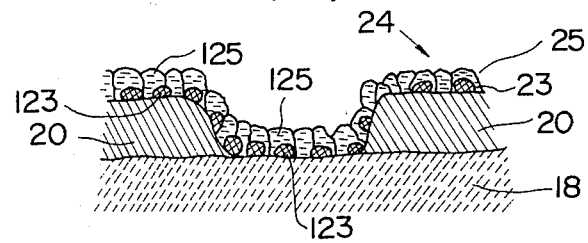

By performing the second stage vacuum evaporation operation to deposit the outer layer 25 on the inner layer 23 having the island structure of FIG. 11(A) the outer layer 25 can be obtained as an agglomeration of small columns 125 as shown in FIG. 12(A), because the tiny grains 123 of the inner layer 23 serve as nuclei for the respective columns 125. The second measurement electrode layer 24 of FIG. 12(A) and an oxygen sensing element having this electrode layer 24 exhibit the same advantages as explained above with reference to FIG. 10(A).

Figure 11B:
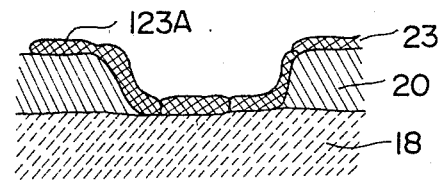
Figure 12B:
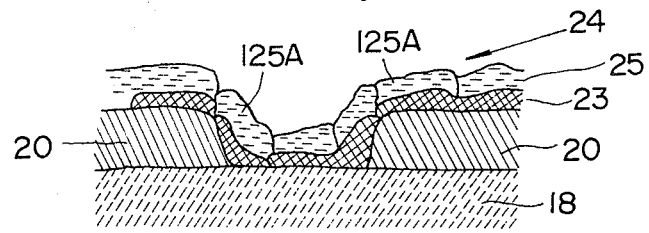
Figure 13A:
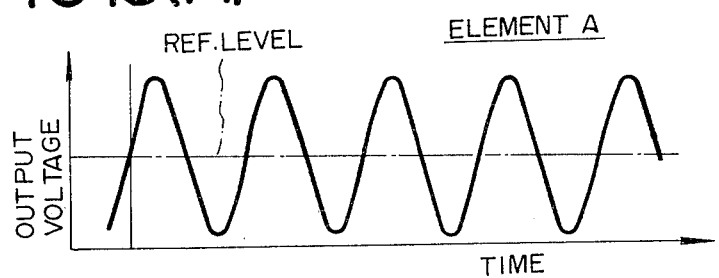
FIGS. 13(A) to 13(D) are charts for comparison of output characteristics of three oxygen sensing elements slightly differently produced in accordance with the present invention and a resembling oxygen sensing element produced not in accordance with the invention in an engine exhaust gas.
Figure 13B:
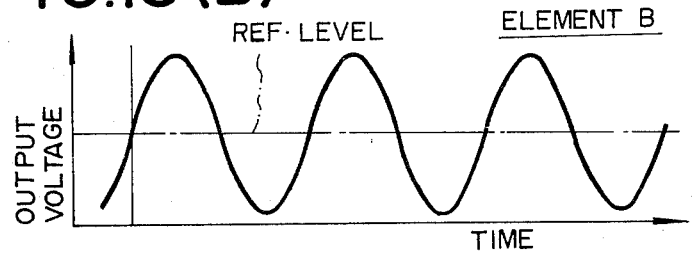
Figure 13C:
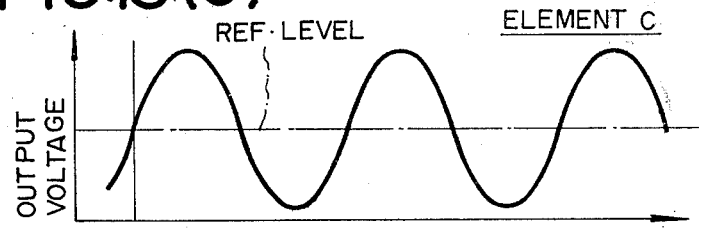
Figure 13D:
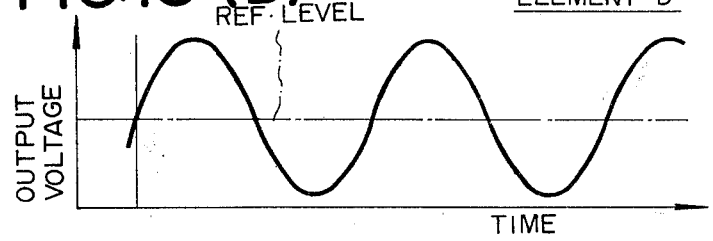

When the second stage evaporation operation is performed to deposit the outer layer 25 on the inner layer 123A of FIG. 11(B), the outer layer 25 becomes an agglomeration of considerably large columnar regions 125A as shown in FIG. 12(B). The addition of the second measurement electrode layer 24 of FIG. 12(B) to the usual first measurement electrode layer 20 brings about a certain increase in the triple-phase points but, in practice, does not remarkably improve the responsiveness of the oxygen sensing element.

Even in the desirable case of FIG. 12(A), the vacuum evaporation deposition of the outer layer 25 is terminated preferably before the total thickness of the second measurement electrode layer (23+25) exceeds 1.0 micron for the same reason as explained regarding the sputtering method.

EXPERIMENT 1

This experiment was carried out on the following four kinds of oxygen sensing elements.

Element A: the element 10A of FIG. 2 produced in Example 1, of which the second measurement electrode layer 24 (23+25) of platinum was formed by the two-stage ion plating process to a total thickness of 0.8 microns.

Element B: the element 10 of FIG. 1 produced generally in accordance with Example 1, but the second measurement electrode layer 24 was formed by single-stage ion plating of platinum to a thickness of 0.8 microns.

Element C: the element of FIG. 1 produced similarly to the Element B, but the second measurement electrode layer 24 had a thickness of 1.5 microns.

Element D: the element 40 of FIG. 4 produced generally in accordance with Example 1, but the second measurement electrode layer was not formed.

These oxygen sensing elements were individually installed in an exhaust pipe of a 1.8-liter automotive gasoline engine as the element of an air/fuel ratio detecting device of the type as shown in FIG. 3, and the fuel supply means for the engine was controlled by a feedback-type control system which produced a fuel-supply-rate control signal based on the result of a comparison between the output voltage of the oxygen sensing element (indicative of an air/fuel ratio realized in the engine) and a reference voltage corresponding to a stoichiometric air/fuel ratio taken as the aim of the control to correct deviations of the actual air/fuel ratio from the stoichiometric ratio. Each oxygen sensing element was operated by forcing a constant DC current of 30 microamperes to flow through the solid electrolyte layer 18 from the reference electrode layer 16 towards the first measurement electrode layer 20, and the engine was operated at a constant rate corresponding to a vehicle speed of 40 km/hr. The charts of FIGS. 13(A), 13(B), 13(C) and 13(D) respectively show the manners of periodic changes in the output voltages of the four kinds of Elements A, B, C and D in this Experiment.

The output voltage of the oxygen sensing element disposed in the exhaust gas becomes above the level of the reference voltage while the actual air/fuel ratio is below the stoichiometric ratio and becomes below the reference level as the control signal commands the fuel supplying means to decrease the rate of fuel supply, and again rises as the control signal reverses its meaning. The control system continues to function so as to converge the periodic fluctuations of the output voltages of the element to the reference level. The quickness of response of each oxygen sensing element is represented by the frequency of the periodic changes shown in the corresponding one of these charts.

As can be seen, the oxygen sensing Element A having the double-layered second measurement electrode layer 24 of an adequate thickness exhibited the highest frequency of changes in its output voltage among the tested four kinds of Elements A, B, C and D, meaning that the Element A was the best in the quickness of response to changes in the actual air/fuel ratio. The frequency of changes exhibited by the Element A was roughly two times as high as that exhibited by the Element D produced by the known method. Furthermore, the Element A was the greatest in the maximal amplitude of the output voltage.

The element B having the second measurement electrode layer 24 of an adequate thickness formed by the single-stage ion plating process was lower in the frequency of output voltage changes than the Element A probably because of a decrease in the triple-phase points, but the frequency of the changes exhibited by the Element B was still about 1.5 times as high as that exhibited by the Element D.

The Element C having the second measurement electrode layer 24 of an excessively large thickness was only slightly better than the Element D in the responsiveness.

As the second part of this Experiment, a catalytic converter containing a conventional three-way catalyst was attached to the exhaust pipe at a location downstream of the oxygen sensing element. The three-way catalyst had the ability of catalyzing both oxidation of CO and HC and reduction of NOx and worked most efficiently in an exhaust gas produced by combustion of a stoichiometric air-fuel mixture. In this case, the engine was operated according to an operating condition pattern specified to simulate travelling of an automobile in urban areas.

Figure 14:
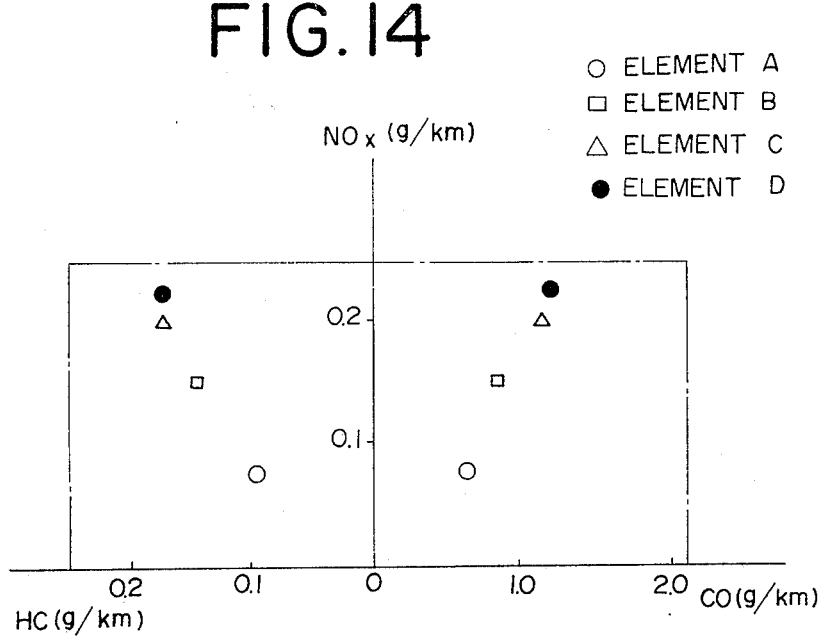
FIG. 14 is a chart showing variations in the performance of an automotive engine exhaust gas purifying system observed when the four oxygen sensing elements mentioned regarding FIGS. 13(A) to 13(D) were alternately used in this system.

The chart of FIG. 14 shows the CO, HC and NOx emission values measured in this Experiment for the four kinds of oxygen sensing Elements A, B, C and D. Each value shown in this chart is an average of actual data obtained for 10 samples of each kind of Element.

Also in this case, the Element A gave the outstandingly best result. The Element B gave a considerably better result compared with the Element D not in accordance with the invention, whereas the Element C was barely better than the Element D.

EXPERIMENT 2

This experiment was carried on the following three kinds of oxygen sensing elements.

Element P: the element 10A of FIG. 2 produced in Example 2, of which the second electrode layer 24 (23+25) of platinum was formed by the two-stage sputtering process to a total thickness of 0.8 microns.

Element Q: the element 10 of FIG. 1 produced generally in accordance with Example 2, but the second measurement electrode layer 24 was formed by single-stage sputtering of platinum to a thickness of 1.5 microns.

Element D: the element 40 of FIG. 4 mentioned in Experiment 1.

Figure 15A:
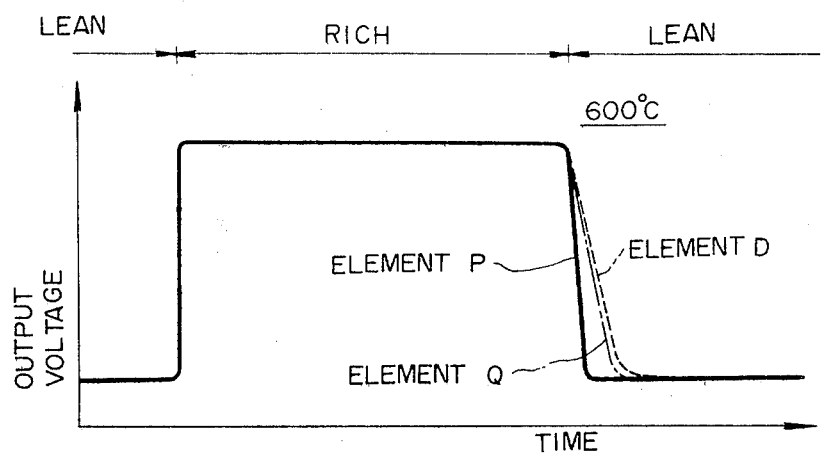
FIG. 15(A) is a chart showing differences in responsiveness of two oxygen sensing elements slightly differently produced in accordance with the invention and a resembling oxygen sensor produced not in accordance with the invention in an engine exhaust gas which undergoes abrupt changes in its oxygen concentration.

These oxygen sensing elements were individually installed in the exhaust pipe of the engine mentioned in Experiment 1 and operated by forcing a constant DC current of 30 microamperes to flow from the reference electrode layer 16 towards the first measurement electrode layer 20 and supplying a controlled heating current to the heater 14 so as to keep the element in the exhaust gas at a constant temperature of 600° C. The engine was alternately supplied with a fuel-rich mixture to produce an exhaust gas containing 3% of CO and a lean mixture to produce an exhaust gas containing 0.3% of CO in order to examine the quickness of response of each oxygen sensing element to a change from the lean mixture to the rich mixture or reversely. First, this experiment was carried out by maintaining the exhaust gas temperature at the location of the oxygen sensing element constantly at 600° C. The results are shown in FIG. 15(A).

As can be seen, the Element P having the double-layered second measurement electrode layer 24 of an adequate thickness was considerably better in responsiveness than the Element D not having the second measurement electrode layer, whereas the Element Q having the second measurement electrode layer 24 of an excessively large thickness was barely better in responsiveness than the Element D.

Figure 15B:
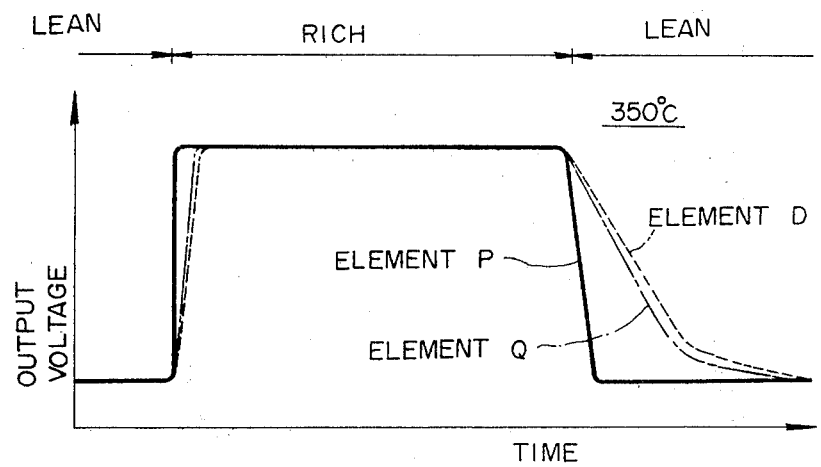
FIG. 15(B) is a chart showing the same matter as FIG. 15(A) but under a lower exhaust gas temperature condition.

Then the same experiment was carried out by lowering the exhaust gas temperature at the location of the oxygen sensing element to 350° C., and the results are shown in FIG. 15(B). The exhaust gas temperature was varied since it had been known that even though the oxygen sensing element itself is maintained at a constant temperature by the action of the heater 14 the performance of the element is affected by the exhaust gas temperature because of changes in the rate of heat radiation from or to the element.

At this exhaust gas temperature, every one of the Elements P, Q and D exhibited deterioration in its responsiveness compared with the performance in the 600° C. exhaust gases, but it can be seen that the Element P was distinctly smaller in the scale of the deterioration than the Examples Q and D. This is a demonstration of an improvement in the temperature dependence of the oxygen sensing element produced by the present invention.

EXPERIMENT 3

This experiment was similar to Experiment 1 and carried out on the following three kinds of oxygen sensing elements.

Element S: the element 10A of FIG. 2 produced in Example 3, of which the second measurement electrode layer 24 (23+25) of platinum was formed by the two-stage vacuum evaporation process to a total thickness of 0.8 microns.

Element T: the element 10 of FIG. 1 produced generally in accordance with Example 3, but the second measurement electrode layer 24 was formed by single-stage vacuum evaporation of platinum to a thickness of 1.5 microns.

Element D: the element 40 of FIG. 4 mentioned in Experiment 1.

Figure 16A:
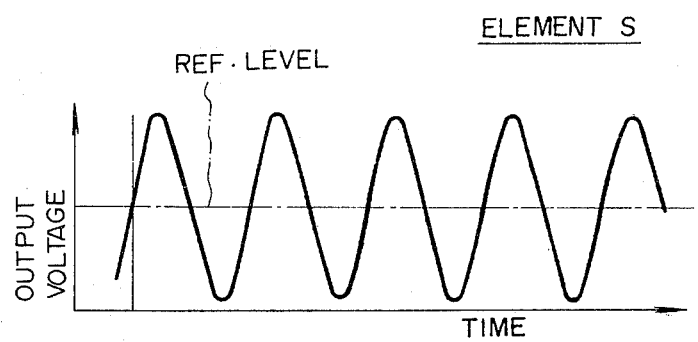
FIGS. 16(A) to 16(C) are charts for comparison of output characteristics of two oxygen sensing elements slightly different produced in accordance with the invention and a resembling oxygen sensing element produced not in accordance with the invention in an engine exhaust gas.
Figure 16B:
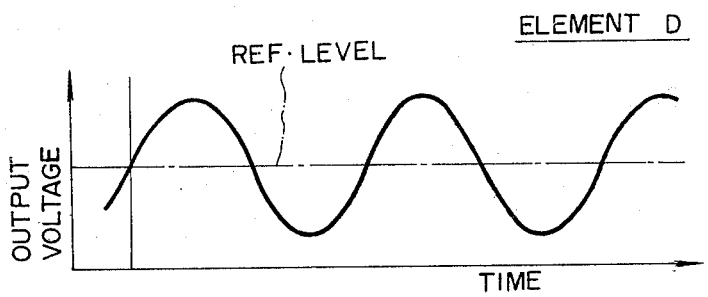
Figure 16C:
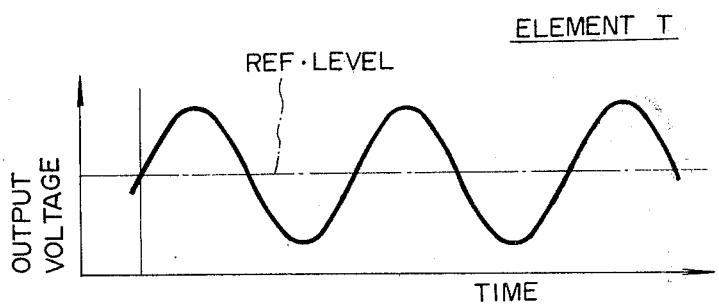

FIGS. 16(A), 16(B) and 16(C) show the results of Experiment 3 for the Elements S, D and T, respectively.

As for the responsiveness represented by the frequency of periodic changes of the output voltage, the Element S was about two times as high as the Element D not having the second measurement electrode layer. The Element S was the best also in the maximal amplitude of the output voltage. The Element T having the thick second measurement electrode layer, too, was better in responsiveness than the Element D, but the improvement attained by this Element T was very small.

Figure 17:
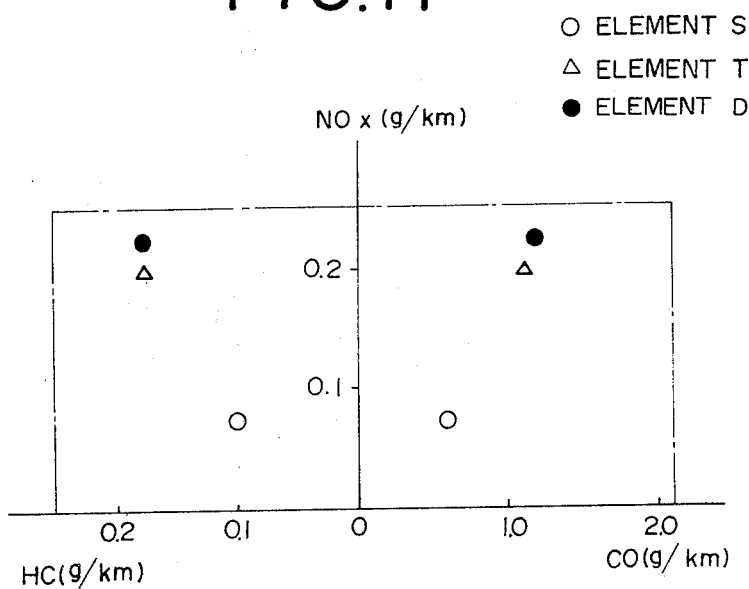
FIG. 17 is a chart showing the same matter as FIG. 14 but with respect to the three oxygen sensing elements mentioned regarding FIGS. 16(A) to 16(C).

As the second part of this Experiment, the effects of these Elements S, T and D on the efficiencies of the three-way catalyst were examined by the method described in Experiment 1. The results are shown in FIG. 17. As can be seen, also in this case the Element S having a double-layered and suitably thin second measurement electrode layer 24 allowed the three-way catalyst to exhibit remarkably enhanced conversion efficiencies for all of CO, HC and NOx.

EXPERIMENT 4

This experiment was carried out to confirm the effect of the sputter-etching described hereinbefore with respect to the formation of the second measurement electrode layer 24 by vacuum evaporation on the durability of the second measurement electrode layer 24. The following two kinds of oxygen sensing elements were subjected to this experiment.

Element S: the element 10A of FIG. 2 produced in Example 3 by forming the second measurement electrode layer 24 (23+25) by the two-stage vacuum evaporation process including the preparatory sputter-etching procedure. Element U: generally similar to the Element S except only that the sputter-etching procedure was omitted in the production of this Element U.

This experiment was a sort of endurance test. The Elements S and U were maintained in a stream of a simulated exhaust gas which contained 5% of CO, had a constant temperature of 800° C. and flowed at a constant velocity of 200 m/sec. The Elements S and U were taken out of the exhaust stream at intervals of 50 hours and subjected to visual observation under a magnifying glass to examine the state of the protecting layer 26 formed on the second measurement electrode layer 24.

For the Element S (ten samples), no changes were observed even after continuation of the test for 200 hours. The Element U (ten samples), too, exhibited no changes when observed after the lapse of 50 hours from the start of the test. After the lapse of additional 50 hours, however, cracks were found in the protecting layer 26 of the Element U, and this protecting layer 26 was separating from the essential part of the element in certain areas. After another 50 hours (150 hours from the start), it was observed that the protecting layer 26 of the Element U had almost entirely peeled off. By observation under a microscope, it was confirmed that the peeling had occurred at the interface between the second measurement electrode layer 24 and the sintered first measurement electrode layer 20.

The results of this experiment demonstrate that the strength of adhesion of the second measurement electrode layer 24 formed by vacuum evaporation can greatly be enhanced by performing the above described sputter-etching procedure in advance.

What is claimed is:

1. A method of producing an oxygen sensing element of the concentration cell type, the method comprising the steps of:

preparing a lamination of a shield layer made of a ceramic material, a reference electrode layer laid on a major surface of said shield layer, an oxygen ion conductive solid electrolyte layer formed on said surface of said shield layer such that said reference electrode layer is tightly sandwiched between said shield layer and said solid electrolyte layer and a first measurement electrode layer which has a microscopically porous and gas-permeable structure and is formed on and in close contact with the outer surface of said solid electrolyte layer by applying a wet composition containing fine particles of a metal onto said surface of said solid electrolyte layer, drying the applied composition to evaporate the liquid component of the applied composition and firing the uncompleted lamination to sinter the metal particles contained in the applied composition;

and forming a second measurement electrode layer having a microscopically porous and gas-permeable structure on the outer surface of said first measurement electrode layer by physical vapor deposition of a metal on said surface of said first measurement electrode layer, wherein said forming of said second measurement electrode layer comprises a first sub-step of performing said physical vapor deposition for a limited time such that the thickness of a metal film on said lamination during said first sub-step does not exceed 0.5 microns, a second sub-step of subjecting said lamination with said metal film deposited thereon from said first sub-step to a heat treatment performed in air at a temperature in the range from 900° to 1100° C. and a third sub-step of resuming said physical vapor deposition wherein said metal film subjected to said heat treatment becomes an innermost part of said second measurement electrode layer.

2. A method according to claim 1, wherein said second measurement electrode layer is formed so as to have a thickness not greater than 1.0 micron.

3. A method according to claim 2, wherein the material for said second measurement electrode layer is a metal which is electronically conducting and can catalyze oxidation reactions of carbon monoxide and hydrocarbons.

4. A method according to claim 3, wherein said material for said second measurement electrode layer is selected from the group consisting of metals of the platinum group and alloys containing a metal of the platinum group.

5. A method according to claim 2, wherein said second measurement electrode layer is formed by a sputtering process.

6. A method according to claim 2, wherein said second measurement electrode layer is formed by a vacuum evaporation process.

7. A method according to claim 6, wherein said physical vapor deposition is performed in an inert gas atmosphere maintained at a pressure in the range from $2\times10^{-3}$ to $1\times10^{-2}$ Torr.

8. A method according to claim 6, wherein the step of forming said second measurement electrode layer further comprises renewing the outer surface of said first measurement electrode layer by sputter-etching in advance of said first sub-step.

9. A method according to claim 8, wherein the sputtering-etching step is performed in an oxygen-containing gas atmosphere maintained at a pressure in the range from $2\times10^{-3}$ to $1\times10^{-2}$ Torr.

10. A method according to claim 1, further comprising the step of providing a heating element in said shield layer for heating the oxygen-sensing element to promote oxygen ion conductivity.

11. A method according to claim 10, wherein said heating element comprises a thin wire or thin layer of an electrically resistive material.

12. A method according to claim 10, wherein said shield layer comprises an upper and lower portion wherein said heating element is located between said upper and lower portions.

13. A method according to claim 3, wherein said second measurement electrode layer is formed by a multi-stage physical vapor deposition process consisting of at least three stages performed with time intervals between the respective stages of said multi-stage deposition process, the first step of said multi-stage process being terminated before the thickness of an innermost layer of said second measurement electrode layer deposited by said first stage exceeds 0.5 microns.

14. A method according to claim 3, wherein the material for said first measurement electrode layer is a metal which is electronically conducting and can catalyze oxidation reactions of carbon monoxide and hydrocarbons.

15. A method according to claim 14, wherein the material for said reference electrode layer is a metal which is electronically conducting and can catalyze oxidation reactions of carbon monoxide and hydrocarbons.

16. A method according to claim 14, wherein the material for said reference electrode layer is an electronically conducting mixture of a metal and an oxide thereof.

17. A method according to claim 1, further comprising the step of subjecting said lamination to ultrasonic cleaning in an organic solvent prior to the step of forming said second measurement electrode layer.

18. A method according to claim 1, further comprising the step of forming a porous protecting layer at least on the outer surface of said second measurement electrode layer.

* * * * *